United States Patent
Beraud et al.

(12) 
(10) Patent No.: US 6,379,912 B1
(45) Date of Patent: Apr. 30, 2002

(54) MOTOR PROTEINS AND METHOD FOR THEIR USE

(75) Inventors: Christophe Beraud, San Francisco; Roman Sakowicz; Kenneth W. Wood, both of Foster City, all of CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 09/723,262

(22) Filed: Nov. 27, 2000

Related U.S. Application Data

(63) Continuation of application No. 09/572,191, filed on May 17, 2000.

(51) Int. Cl.⁷ .............................. C12Q 1/44; C12N 9/16
(52) U.S. Cl. ......................................... 435/19; 435/196
(58) Field of Search .................................... 435/19, 196

(56) References Cited

PUBLICATIONS

Boleti et al. (1996) "Xklp2, a novel Xenopus centrosomal kinesin–like protein required for centrosome separation during mitosis" Cell 84:49–59.

Nakagawa et al. (1997) "Identification and classification of 16 new kinesin superfamily (KIF) proteins in mouse genome" Proc Natl Acad Sci U S A 94:9654–9.

Wittmann et al. (1998) "Localization of the kinesin–like protein Xklp2 to spindle poles requires a leucine zipper, a microtubule–associated protein, and dynein" J Cell Biol 143:673–85.

Walczak et al. (1998) "A model for the proposed roles of different microtubule–based motor proteins in establishing spindle bipolarity" Curr Biol 8:903–13.

Sueishi et al. (2000) "The forkhead–associated domain of Ki–67 antigen interacts with the novel kinesin–like protein Hkllp2" J. Biol. Chem. 275:28888–28892.

GenBank, Accession No. AB035898, Direct Submission, Hkpl2 mRNA for kinesin–like protein 2, (2000).

*Primary Examiner*—Rebecca E. Prouty
(74) *Attorney, Agent, or Firm*—Lauren L. Stevens, Esq.; Beyer Weaver & Thomas LLP

(57) ABSTRACT

The invention provides isolated nucleic acid and amino acid sequences of HsKif15, antibodies to HsKif15, methods of screening for HsKif15 modulators using biologically active HsKif15, and kits for screening for HsKif15 modulators.

16 Claims, 8 Drawing Sheets

FIG. 1A

```
   1 ATGGCACCCG GCTGCAAAAC TGAGTTACGC AGCGTGACAA ATGGTCAGTC
  51 TAACCAACCA AGTAATGAAG GTGATGCCAT CAAAGTTTTT GTGCGAATTC
 101 GTCCTCCTGC AGAAAGATCT GGGTCAGCTG ATGGAGAGCA GAACTTATGC
 151 TTATCTGTGC TGTCCTCCAC GAGTCTCCGG CTGCACTCCA ACCCTGAGCC
 201 CAAGACCTTC ACGTTTGATC ATGTTGCAGA TGTGGATACC ACTCAGGAAT
 251 CTGTATTCGC AACTGTGGCT AAAAGCATTG TGGAGTCTTG CATGAGCGGT
 301 TATAATGGTA CCATCTTTGC ATATGGACAG ACTGGCTCAG GGAAGACATT
 351 TACTATGATG GGACCATCTG AATCTGATAA TTTTTCTCAT AACCTGAGAG
 401 GAGTAATCCC ACGAAGTTTT GAATATTTGT TTTCCTTAAT TGATCGTGAA
 451 AAAGAAAGG CTGGAGCTGG AAAGAGTTTC CTTTGTAAGT GTTCCTTTAT
 501 TGAAATCTAC AACGAGCAGA TATATGATCT ACTGGACTCT GCATCGGCTG
 551 GACTGTACTT AAGGGAGCAT ATCAAGAAGG GAGTCTTTGT TGTTGGTGCG
 601 GTGGAGCAGG TGGTAACCTC AGCTGCTGAA GCCTATCAGG TGTTGTCTGG
 651 AGGATGGAGG AATAGACGTG TGGCATCAAC ATCAATGAAC AGAGAATCGT
 701 CTAGGTCTCA TGCCGTCTTT ACAATTACAA TAGAGTCAAT GGAGAAAAGT
 751 AATGAGATTG TGAATATACG GACCTCCCTA CTCAACCTGG TGGATTTAGC
 801 AGGATCTGAA AGGCAAAAAG ATACCCATGC AGAAGGGATG AGATTGAAGG
 851 AAGCAGGTAA CATAAATCGA TCATTGAGCT GCCTGGGCCA AGTGATTACA
 901 GCACTTGTCG ACGTGGGTAA TGGAAAACAG AGACATGTTT GCTACAGAGA
 951 CTCCAAACTT ACCTTCTTAC TACGGGATTC CCTTGGAGGT AATGCCAAAA
1001 CAGCCATAAT TGCAAATGTT CATCCTGGAT CCAGGTGTTT TGGGGAAACC
1051 CTATCAACAC TTAACTTTGC TCAAAGAGCC AAGCTGATTA AAAACAAGGC
1101 AGTAGTAAAT GAAGACACCC AAGGAAATGT GAGCCAGCTC CAAGCTGAAG
1151 TGAAGAGGCT CAAAGAACAA CTGGCGGAGC TTGCTTCAGG ACAGACACCA
1201 CCAGAAAGCT TCCTGACCAG AGACAAAAAG AAGACTAACT ATATGGAGTA
1251 TTTCCAGGAA GCAATGTTAT TCTTTAAGAA ATCTGAACAG GAAAAGAAGT
1301 CTCTGATAGA AAAAGTTACC CAATTAGAAG ACCTCACCCT CAAAAAGGAA
1351 AAATTTATTC AATCTAATAA AATGATTGTG AAATTCGAG AGGATCAAAT
1401 AATACGCTTG GAAAAGCTCC ACAAGGAATC CGGGGAGGT TTTCTGCCTG
1451 AGGAGCAGGA TCGTTTGCTC TCAGAATTAA GGAATGAGAT TCAAACTCTG
1501 CGAGAACAAA TAGAGCACCA CCCCAGAGTT GCAAAGTATG CTATGGAAAA
1551 TCATTCCCTC AGGGAGGAGA ATAGAAGACT GAGATTATTA GAGCCTGTGA
1601 AAAGAGCTCA AGAAATGGAT GCCCAGACCA TTGCAAAACT AGAAAAAGCT
1651 TTCTCTGAAA TAAGTGGCAT GGAGAAAAGT GACAAAAATC AGCAAGGATT
1701 TTCACCTAAA GCTCAGAAAG AGCCATGTTT GTTTGCAAAC ACTGAGAAGT
1751 TAAAAGCACA ACTCCTGCAA ATTCAGACAG AGCTGAATAA TTCAAAGCAA
1801 GAATATGAAG AATTCAAAGA ACTTACTAGG AAAAGGCAGC TAGAATTGGA
1851 ATCAGAGCTT CAGTCTTTGC AAAAAGCGAA CCTTAATCTT GAAAACCTTT
1901 TGGAAGCAAC AAAAGCCTGC AAGCGGCAAG AAGTTTCTCA GCTGAATAAA
1951 ATTCATGCTG AAACACTTAA GATTATAACT ACACCAACCA AGGCCTACCA
2001 ACTTCATTCC CGACCAGTAC CAAAATTAAG CCCTGAAATG GGAAGCTTTG
2051 GCTCTCTATA CACTCAGAAT TCTAGCATAT TAGATAATGA TATATTAAAT
2101 GAGCCAGTTC CTCCTGAGAT GAATGAACAA GCTTTTGAGG CCATTTCTGA
2151 AGAGCTTAGA ACAGTGCAGG AACAAATGAG TGCTCTTCAA GCCAAACTGG
```

FIG. 1B

```
2201 ATGAAGAAGA GCATAAAAAC CTAAAGCTTC AGCAGCATGT TGACAAACTG
2251 GAACATCATT CTACCCAAAT GCAGGAGCTT TTCTCATCAG AAAGAATTGA
2301 TTGGACCAAA CAGCAGGAAG AGCTTCTCTC ACAGTTGAAT GTCCTTGAAA
2351 AGCAGCTTCA AGAGACTCAA ACTAAAAATG ACTTTTTGAA AAGTGAGGTA
2401 CATGACCTGC GAGTAGTCCT TCATTCTGCT GACAAGGAGC TTTCTTCAGT
2451 GAAATTGGAA TATAGTTCAT TCAAACGAA TCAGGAGAAA GAATTCAACA
2501 AACTTTCCGA AGACACATG CATGTACAGC TTCAATTAGA TAATCTCAGG
2551 TTAGAAAACG AAAAGCTGCT TGAGAGCAAA GCCTGCCTAC AGGATTCCTA
2601 TGACAACTTA CAAGAAATAA TGAAATTTGA GATTGACCAA CTTTCAAGAA
2651 ACCTCCAAAA CTTCAAAAAA GAAAATGAAA CTCTGAAATC TGATCTGAAT
2701 AATTTGATGG AGCTTCTTGA GGCAGAAAAA GAACGCAATA ACAAATTATC
2751 ATTACAGTTT GAAGAAGATA AGAAAACAG TTCTAAAGAA ATCTTAAAAG
2801 TTCTTGAGGC TGTACGTCAG GAGAAACAGA AGAGACGGC CAAGTGTGAG
2851 CAGCAGATGG CAAAAGTACA GAAACTAGAA GAGAGCTTGC TTGCTACTGA
2901 AAAAGTGATC AGTTCCCTGG AAAAGTCTAG AGATTCTGAT AAGAAAGTTG
2951 TAGCTGACCT CATGAACCAG ATCCAGGAGC TAAGATCATC GGTCTGTGAG
3001 AAAACAGAAA CTATAGACAC CCTGAAACAA GAACTGAAGG ACATAAATTG
3051 CAAATACAAC TCTGCTTTGG TTGACAGAGA AGAGAGCAGA GTGTTGATCA
3101 AGAAGCAGGA AGTGGATATT CTGGATCTGA AAGAAACCCT TAGGCTGAGA
3151 ATACTTTCTG AGGACATAGA GAGGGATATG CTCTGTGAGG ACCTGGCTCA
3201 TGCCACTGAG CAGCTGAACA TGCTCACAGA GGCCTCAAAA AAACACTCGG
3251 GGCTGCTGCA GTCTGCCCAG GAAGAACTGA CCAAGAAGGA AGCCCTGATT
3301 CAGGAACTTC AGCACAAGCT AAACCAAAAG AAAGAGGAAG TAGAACAGAA
3351 GAAGAATGAA TATAACTTCA AAATGAGGCA ACTAGAACAT GTGATGGATT
3401 CTGCTGCTGA GGATCCCCAG AGTCCTAAGA CACCACCTCA CTTTCAAACA
3451 CATTTGGCAA AACTCCTGGA ACACAAGAA CAAGAGATAG AAGATGGAAG
3501 AGCCTCTAAG ACTTCTTTGG AACACCTTGT AACAAAGCTA AATGAAGACA
3551 GAGAAGTCAA AAATGCTGAA ATCCTCAGAA TGAAGGAGCA GTTGCGTGAA
3601 ATGGAAAACC TACGCCTGGA AAGTCAGCAG TTAATAGAGA AAAACTGGCT
3651 CCTGCAAGGT CAGCTGGATG ATATTAAAAG ACAAAAGGAA AACAGTGATC
3701 AGAATCATCC AGATAATCAA CAGCTGAAGA ATGAACAAGA AGAAAGTATC
3751 AAAGAAAGAC TTGCAAAAAG TAAATAGTT GAAGAAATGC TGAAAATGAA
3801 AGCAGACCTA GAAGAAGTCC AAAGTGCCCT TTACAACAAA GAGATGGAAT
3851 GCCTTAGAAT GACTGATGAA GTCGAACGAA CCCAAACTTT GGAGTCTAAA
3901 GCATTCCAGG AAAAAGAACA ACTGAGATCA AGCTGGAAG AAATGTATGA
3951 AGAAAGAGAG AGAACATCCC AGGAGATGGA AATGTTAAGG AAGCAGGTGG
4001 AGTGTCTTGC TGAGGAAAAT GGAAAGTTGG TAGGTCACCA AAATTTGCAT
4051 CAGAAGATTC AGTACGTAGT GCGACTAAAG AAGGAAAATG TCAGGCTTGC
4101 TGAGGAGACA GAAAAGTTGC GTGCCGAAAA TGTATTTTA AAAGAAAAGA
4151 AAAGAAGTGA ATCTTGAGGA TTCCGGTCAG CTACCTAGGC ATCACCTTGT
4201 TTGAAGATGT TTCTTCTCTT TTACAAGTAA GACCTACTCC TGGCCACTTA
4251 GGAGAGCTGA ATTTATGGAC CTTAATTATT AAATGTTTAT AAGGTGGTGG
4301 TAACCACCTC AAGTTTCTGA TGACATTCT GCATCCATAT ACACCCTGTG
4351 ACAGTCAGCA GTCTGCTATT AAGTGGCCTA CTTCAAGGCT TTGAATCAAC
4401 TTAAGGGAAA ACCTTTTGTC TTTGTAAAAA TAAAAGCCTG TAGCTAAGGT
```

FIG. 1C

```
4451 TTACAGTGGA CATTAGCCAG ATCATTTTCT TCTTAGATTA TGCCATAATC
4501 TCCTTTGATT CTTATGGAAG TTCTAACAAT ATATGGTGGT TCCAACACCT
4551 GCAGTGAGTT TAATGACTGA CTTAGTAGCA GGTACAAGAA GCAAACTTGT
4601 TAATATAGAT TATTTTGTA TTCTTACTTT AGGTATTTTC TTGAGCATTT
4651 TCCATGACTG TAAATAAAGC CATTTTTTAA GATAATAAAA AAAAAAAAA
4701 AAAACTCGAG GGGGGGCCCG GTACCCAATT CGCCCTATAG TGAGTCGTAT
4751 TACAATC
```

FIG. 2

```
   1  MAPGCKTELR SVTNGQSNQP SNEGDAIKVF VRIRPPAERS GSADGEQNLC
  51  LSVLSSTSLR LHSNPEPKTF TFDHVADVDT TQESVFATVA KSIVESCMSG
 101  YNGTIFAYGQ TGSGKTFTMM GPSESDNFSH NLRGVIPRSF EYLFSLIDRE
 151  KEKAGAGKSF LCKCSFIEIY NEQIYDLLDS ASAGLYLREH IKKGVFVVGA
 201  VEQVVTSAAE AYQVLSGGWR NRRVASTSMN RESSRSHAVF TITIESMEKS
 251  NEIVNIRTSL LNLVDLAGSE RQKDTHAEGM RLKEAGNINR SLSCLGQVIT
 301  ALVDVGNGKQ RHVCYRDSKL TFLLRDSLGG NAKTAIIANV HPGSRCFGET
 351  LSTLNFAQRA KLIKNKAVVN EDTQGNVSQL QAEVKRLKEQ LAELASGQTP
 401  PESFLTRDKK KTNYMEYFQE AMLFFKKSEQ EKKSLIEKVT QLEDLTLKKE
 451  KFIQSNKMIV KFREDQIIRL EKLHKESRGG FLPEEQDRLL SELRNEIQTL
 501  REQIEHHPRV AKYAMENHSL REENRRLRLL EPVKRAQEMD AQTIAKLEKA
 551  FSEISGMEKS DKNQQGFSPK AQKEPCLFAN TEKLKAQLLQ IQTELNNSKQ
 601  EYEEFKELTR KRQLELESEL QSLQKANLNL ENLLEATKAC KRQEVSQLNK
 651  IHAETLKIIT TPTKAYQLHS RPVPKLSPEM GSFGSLYTQN SSILDNDILN
 701  EPVPPEMNEQ AFEAISEELR TVQEQMSALQ AKLDEEEHKN LKLQQHVDKL
 751  EHHSTQMQEL FSSERIDwTK QQEELLSQLN VLEKQLQETQ TKNDFLKSEV
 801  HDLRVVLHSA DKELSSVKLE YSSFKTNQEK EFNKLSERHM HVQLQLDNLR
 851  LENEKLLESK ACLQDSYDNL QEIMKFEIDQ LSRNLQNFKK ENETLKSDLN
 901  NLMELLEAEK ERNNKLSLQF EEDKENSSKE ILKVLEAVRQ EKQKETAKCE
 951  QQMAKVQKLE ESLLATEKVI SSLEKSRDSD KKVVADLMNQ IQELRSSVCE
1001  KTETIDTLKQ ELKDINCKYN SALVDREESR VLIKKQEVDI LDLKETLRLR
1051  ILSEDIERDM LCEDLAHATE QLNMLTEASK KHSGLLQSAQ EELTKKEALI
1101  QELQHKLNQK KEEVEQKKNE YNFKMRQLEH VMDSAAEDPQ SPKTPPHFQT
1151  HLAKLLETQE QEIEDGRASK TSLEHLVTKL NEDREVKNAE ILRMKEQLRE
1201  MENLRLESQQ LIEKNWLLQG QLDDIKRQKE NSDQNHPDNQ QLKNEQEESI
1251  KERLAKSKIV EEMLKMKADL EEVQSALYNK EMECLRMTDE VERTQTLESK
1301  AFQEKEQLRS KLEEMYEERE RTSQEMEMLR KQVECLAEEN GKLVGHQNLH
1351  QKIQYVVRLK KENVRLAEET EKLRAENVFL KEKKRSES
```

FIG. 3

```
   1 ATGGCACCCG GCTGCAAAAC TGAGTTACGC AGCGTGACAA ATGGTCAGTC
  51 TAACCAACCA AGTAATGAAG GTGATGCCAT CAAAGTTTTT GTGCGAATTC
 101 GTCCTCCTGC AGAAAGATCT GGGTCAGCTG ATGGAGAGCA GAACTTATGC
 151 TTATCTGTGC TGTCCTCCAC GAGTCTCCGG CTGCACTCCA ACCCTGAGCC
 201 CAAGACCTTC ACGTTTGATC ATGTTGCAGA TGTGGATACC ACTCAGGAAT
 251 CTGTATTCGC AACTGTGGCT AAAAGCATTG TGGAGTCTTG CATGAGCGGT
 301 TATAATGGTA CCATCTTTGC ATATGGACAG ACTGGCTCAG GGAAGACATT
 351 TACTATGATG GGACCATCTG AATCTGATAA TTTTTCTCAT AACCTGAGAG
 401 GAGTAATCCC ACGAAGTTTT GAATATTTGT TTCCTTAAT TGATCGTGAA
 451 AAAGAAAAGG CTGGAGCTGG AAAGAGTTTC CTTTGTAAGT GTTCCTTTAT
 501 TGAAATCTAC AACGAGCAGA TATATGATCT ACTGGACTCT GCATCGGCTG
 551 GACTGTACTT AAGGGAGCAT ATCAAGAAGG GAGTCTTTGT TGTTGGTGCG
 601 GTGGAGCAGG TGGTAACCTC AGCTGCTGAA GCCTATCAGG TGTTGTCTGG
 651 AGGATGGAGG AATAGACGTG TGGCATCAAC ATCAATGAAC AGAGAATCGT
 701 CTAGGTCTCA TGCCGTCTTT ACAATTACAA TAGAGTCAAT GGAGAAAAGT
 751 AATGAGATTG TGAATATACG GACCTCCCTA CTCAACCTGG TGGATTTAGC
 801 AGGATCTGAA AGGCAAAAAG ATACCCATGC AGAAGGGATG AGATTGAAGG
 851 AAGCAGGTAA CATAAATCGA TCATTGAGCT GCCTGGGCCA AGTGATTACA
 901 GCACTTGTCG ACGTGGGTAA TGGAAAACAG AGACATGTTT GCTACAGAGA
 951 CTCCAAACTT ACCTTCTTAC TACGGGATTC CCTTGGAGGT AATGCCAAAA
1001 CAGCCATAAT TGCAAATGTT CATCCTGGAT CCAGGTGTTT TGGGGAAACC
1051 CTATCAACAC TTAACTTTGC TCAAAGAGCC AAGCTGATTA AAAACAAGGC
1101 ACTCGAGCAC CACCACCACC ACCACTGA
```

FIG. 4

```
  1    MAPGCLTELR SVTNGQSNQP SNEGDAIKVF VRIRPPAERS GSADGEQNLC
 51    LSVLSSTSLR LHSNPEPKTF TFDHVADVDT TQESVFATVA KSIVESCMSG
101    YNGTIFAYGQ TGSGKTFTMM GPSESDNFSH NLRGVIPRSF EYLFSLIDRE
151    KELAGAGLSF LCKCSFIEIY NEQIYDLLDS ASAGLYLREH IKKGVFVVGA
201    VEQVVTSAAE AYQVLSGGWR NRRVASTSMN RESSRSHAVF TITIESMEKS
251    NEIVNIRTSL LNLVDLAGSE RQLDTHAEGM RLKEAGNINR SLSCLGNVIT
301    ALVDVGNGKQ RHVCYRDSKL TFLLRDSLGG NAKTAIKANV HPGSRCFGET
351    LSTLNFAQRA KLIKNKALEH HHHHH
```

FIG. 5

```
1     ATGGCACCCG GCTGCAAAAC TGAGTTACGC AGCGTGACAA ATGGTCAGTC
51    TAACCAACCA AGTAATGAAG GTGATGCCAT CAAAGTTTTT GTGCGAATTC
101   GTCCTCCTGC AGAAAGATCT GGGTCAGCTG ATGGAGAGCA GAACTTATGC
151   TTATCTGTGC TGTCCTCCAC GAGTCTCCGG CTGCACTCCA ACCCTGAGCC
201   CAAGACCTTC ACGTTTGATC ATGTTGCAGA TGTGGATACC ACTCAGGAAT
251   CTGTATTCGC AACTGTGGCT AAAAGCATTG TGGAGTCTTG CATGAGCGGT
301   TATAATGGTA CCATCTTTGC ATATGGACAG ACTGGCTCAG GGAAGACATT
351   TACTATGATG GGACCATCTG AATCTGATAA TTTTTCTCAT AACCTGAGAG
401   GAGTAATCCC ACGAAGTTTT GAATATTTGT TTTCCTTAAT TGATCGTGAA
451   AAAGAAAAGG CTGGAGCTGG AAAGAGTTTC CTTTGTAAGT GTTCCTTTAT
501   TGAAATCTAC AACGAGCAGA TATATGATCT ACTGGACTCT GCATCGGCTG
551   GACTGTACTT AAGGGAGCAT ATCAAGAAGG GAGTCTTTGT TGTTGGTGCG
601   GTGGAGCAGG TGGTAACCTC AGCTGCTGAA GCCTATCAGG TGTTGTCTGG
651   AGGATGGAGG AATAGACGTG TGGCATCAAC ATCAATGAAC AGAGAATCGT
701   CTAGGTCTCA TGCCGTCTTT ACAATTACAA TAGAGTCAAT GGAGAAAAGT
751   AATGAGATTG TGAATATACG GACCTCCCTA CTCAACCTGG TGGATTTAGC
801   AGGATCTGAA AGGCAAAAAG ATACCCATGC AGAAGGGATG AGATTGAAGG
851   AAGCAGGTAA CATAAATCGA TCATTGAGCT GCCTGGGCCA AGTGATTACA
901   GCACTTGTCG ACGTGGGTAA TGGAAAACAG AGACATGTTT GCTACAGAGA
951   CTCCAAACTT ACCTTCTTAC TACGGGATTC CCTTGGAGGT AATGCCAAAA
1001  CAGCCATAAT TGCAAATGTT CATCCTGGAT CCAGGTGTTT TGGGGAAACC
1051  CTATCAACAC TTAACTTTGC TCAAAGAGCC AAGCTGATTA AAAACAAGGC
1101  AGTAGTAAAT GAAGACACCC AAGGAAATGT GAGCCAGCTC CAAGCTGAAG
1151  TGAAGAGGCT CAAAGAACAA CTGGCGGAGC TTGCTTCAGG ACAGACACCA
1201  CCACTCGAGC ACCACCACCA CCACCACTGA
```

FIG. 6

```
  1  MAPGCKTELR SVTNGQSNQP SNEGDAIKVF VRIRPPAERS GSADGEQNLC
 51  LSVLSSTSLR LHSNPEPKTF TFDHVADVDT TQESVFATVA KSIVESCMSG
101  YNGTIFAYGQ TGSGKTFTMM GPSESDNFSH NLRGVIPRSF EYLFSLIDRE
151  KEKAGAGKSF LCKCSFIEIY NEQIYDLLDS ASAGLYLREH IKKGVFVVGA
201  VEQVVTSAAE AYQVLSGGWR NRRVASTSMN RESSRSHAVF TITIESMEKS
251  NEIVNIRTSL LNLVDLAGSE RQKDTHAEGM RLKEAGNINR SLSCLGQVIT
301  ALVDVGNGKQ RHVCYRDSKL TFLLRDSLGG NAKTAIIANV HPGSRCFGET
351  LSTLNFAQRA KLIKNKAVVN EDTQGNVSQL QAEVKRLKEQ LAELASGQTP
401  PLEHHHHHH
```

MOTOR PROTEINS AND METHOD FOR THEIR USE

This application is a continuation of U.S. application Ser. No. 09/572,191, filed May 17, 2000, the disclosure of which is incorporated by reference.

FIELD OF THE INVENTION

The invention provides isolated nucleic acid and amino acid sequences of HsKif15, methods of detecting HsKif15 and screening for HsKif15 modulators using biologically active HsKif15, and kits for screening for HsKif15 modulators.

BACKGROUND OF THE INVENTION

Kinesin defines a ubiquitous, conserved family of over 50 proteins that can be classified into at least 8 subfamilies based on primary amino acid sequence, domain structure, velocity of movement, and cellular function. The kinesin superfamily is an extended family of related microtubule motor proteins. This family is exemplified by "true" kinesin, which was first isolated from the axoplasm of squid, where it is believed to play a role in anterograde axonal transport of vesicles and organelles (see, e.g., Goldstein, *Annu. Rev. Genet.* 27:319–351 (1993)). Kinesin uses ATP to generate force and directional movement associated with microtubules (from the minus to the plus end of the microtubule, hence it is a "plus-end directed" motor). Kinesin superfamily members are defined by a kinesin-like motor that is about 340 amino acids in size and shares approximately 35–45% identity (or more) with the "true" kinesin motor domain. Typically, the motor is attached to a variety of tail domains that provide different binding activities to the various kinesin superfamily members.

Mouse Kif15 (Genbank accession numbers AB001432) was originally identified in a PCR-based search for novel murine kinesins (Nakagawa et al. 1997. Proc Natl Acad Sci U S A 94:9654–9). A portion of the MmKif15 cDNA encoding a fragment of the MmKif15 motor domain was cloned and sequenced. In addition, the mRNA expression of MmKif15 in several tissues from 4 week old mice was examined.

XKlp2 refers to a Xenopus laevis kinesin that has been shown to play an important role in mitotic spindle assembly. XKlp2 was originally identified by Vernos et al. in a PCR-based strategy to clone cDNA fragments encoding novel Xenopus kinesins (Vernos et al. 1993. Dev Biol 157:232–9). The full length sequence of XKlp2 was published by Boleti et al (Boleti et al. 1996. Cell 84:49–59) (Genbank accession numbers B48835, AAB26486, 1587181, and CAA63826). These authors also demonstrated that a recombinant fusion protein containing the motor domain of XKlp2 fused to Glutathione-S-transferase was capable of microtubule-based motility, moving toward microtubule plus ends. Boleti et al found that XKlp2 associates with mitotic spindle poles and with centrosomes, and that addition of recombinant fragments of XKlp2 spanning the C-terminal tail domain caused a dose-dependent inhibition of bipolar spindle assembly in spindle assembly reactions in vitro. Antibodies directed against the C-terminal tail domain of XKlp2 similarly impaired mitotic spindle assembly.

Wittman et al. have demonstrated that the C-terminal tail domain of XKlp2 is necessary and sufficient for localization to microtubule asters assembled in mitotic but not interphase cell extracts (Wittmann et al. 1998. J Cell Biol 143:673–85). This localization required dimerization of the tail domain. In addition, the function of cytoplasmic dynein and dynactin were found to play a role in localization of XKlp2 to the microtubule asters assembled in mitotic cell extracts. Wittman et al also identified a protein, TPX2, that significantly enhanced binding of recombinant XKlp2 tail domain to pure microtubules. It was suggested that TPX2 is the receptor for the tail domain of XKlp2 that mediates interaction with microtubules.

Walczak et al. have examined the role of XKlp2 in formation of bipolar mitotic spindles using mitotic cell extracts and DNA coated magnetic beads (Walczak et al. 1998. Curr Biol 8:903–13). In contrast to the observations of Boleti et al., Walczak et al did not observe significant perturbation of mitotic spindle function upon addition of antibody directed against XKlp2 C-terminal tail domain.

The discovery of a new kinesin motor protein and the polynucleotides encoding it satisfies a need in the art by providing new compositions which are useful in the diagnosis, prevention, and treatment of cancer, neurological disorders, and disorders of vesicular transport.

SUMMARY OF THE INVENTION

The present invention is based on the discovery of a new human kinesin motor protein, HsKif15, the polynucleotides encoding HsKif15, and the use of these compositions for the diagnosis, treatment, or prevention of cancer, neurological disorders, and disorders of vesicular transport.

In one aspect, the invention provides an isolated nucleic acid sequence encoding a kinesin superfamily motor protein, wherein the motor protein has the following properties: (i) the protein's activity includes microtubule stimulated ATPase activity; and (ii) the protein has a sequence that has greater than 70% amino acid sequence identity to SEQ ID NO:2 as measured using a sequence comparison algorithm. In one embodiment, the protein further specifically binds to polyclonal antibodies raised against SEQ ID NO:2.

In one embodiment, the nucleic acid encodes HsKif15 or a fragment thereof. In another embodiment, the nucleic acid encodes SEQ ID NO:2, SEQ ID NO:4, or SEQ ID NO:6. In another embodiment, the nucleic acid has a nucleotide sequence of SEQ ID NO:1, SEQ ID NO:3, or SEQ ID NO:5.

In one aspect, the nucleic acid comprises a sequence which encodes an amino acid sequence which has one or more of the following characteristics:

greater than 70% sequence identity with SEQ ID NO:2, preferably greater than 80%, more preferably greater than 90%, more preferably greater than 95% or, in another embodiment, has 98 to 100% sequence identity with SEQ ID NO:2.

In one embodiment, the nucleic acid comprises a sequence which has one or more of the following characteristics:

greater than 55 or 60% sequence identity with SEQ ID NO:1, preferably greater than 70%, more preferably greater than 80%, more preferably greater than 90 or 95% or, in another embodiment, has 98 to 100% sequence identity with SEQ ID NO: 1. In another embodiment provided herein, the nucleic acid hybridizes under stringent conditions to a nucleic acid having a sequence or complementary sequence of SEQ ID NO: 1.

In another aspect, the invention provides an expression vector comprising a nucleic acid encoding a kinesin superfamily motor protein, wherein the motor protein has the following properties: (i) the protein's activity includes microtubule stimulated ATPase activity; and (ii) the protein has a sequence that has greater than 70% amino acid sequence identity to SEQ ID NO:2 as measured using a sequence comparison algorithm. The invention further provides a host cell transfected with the vector.

In another aspect, the invention provides an isolated kinesin superfamily motor protein, wherein the protein has one or more of the properties described above. In one embodiment, the protein specifically binds to polyclonal antibodies generated against a motor domain, tail domain or other fragment of HsKif15. In another embodiment, the protein comprises an amino acid sequence of SEQ ID NO:2, SEQ ID NO:4, or SEQ ID NO:6.

In one aspect, the protein provided herein comprises an amino acid sequence which has one or more of the following characteristics:
greater than 70% sequence identity with SEQ ID NO:2, preferably greater than 80%, more preferably greater than 90%, more preferably greater than 95% or, in another embodiment, has 98 to 100% sequence identity with SEQ ID NO:2.

The invention features a substantially purified polypeptide comprising the amino acid sequence of SEQ ID NO:2 or a fragment thereof and more particularly, the motor domain of the amino acid sequence of SEQ ID NO:2.

In another aspect, the invention provides a method for screening for modulators of HsKif15, the method comprising the steps of: (i) contacting biologically active motor protein having at least one of properties described above, with at least one candidate agent at a test and control concentration and detecting whether a change in the activity of the motor protein occurs between the test and control concentration, wherein a change indicates a modulator of the motor protein. In one embodiment, the activity is selected from the group consisting of microtubule stimulated ATPase activity and microtubule binding activity. In one embodiment, the method further comprises the step of isolating biologically active HsKif15 from a cell sample. In another embodiment, the biologically active HsKiflS is recombinant.

In another aspect, the invention provides a kit for screening for modulators of HsKif15, the kit comprising; (i) a container holding biologically active HsKif15; and (ii) instructions for assaying for HsKif15 activity, wherein the HsKif15 activity is microtubule binding activity or microtubule stimulated ATPase activity.

BRIEF DESCRIPTION OF THE DRAWINGS

FIGS. 1A, 1B, and 1C show an embodiment of a nucleic acid sequence encoding HsKif15, wherein the start and stop codons are shown underlined and in bold.

FIG. 2 shows the predicted amino acid sequence of HsKif15.

FIG. 3 shows an embodiment of a nucleic acid sequence enecoding HsKif15 motor domain fragment HsKif15M1A367, wherein the start and stop codons are shown underlined and in bold and non-native residues are in bold typeface. The product of the construct was expressed at levels greater than 20 mg/liter of bacterial culture, and was active when purified and assayed for microtubule-stimulated ATPase activity.

FIG. 4 shows the predicted amino acid sequence of HsKif15 motor domain fragment HsKif15M1A367. Residues added to facilitate purification are indicated in bold typeface.

FIG. 5 shows an embodiment of a nucleic acid sequence encoding HsKif15 motor domain fragment HsKif15M1P401, wherein the start and stop codons are shown underlined and in bold and non-native residues are in bold typeface. The product of the construct was expressed at levels greater than 20 mg/liter of bacterial culture, and was active when purified and assayed for microtubule-stimulated ATPase activity.

FIG. 6 shows the predicted amino acid sequence of HsKifl5 motor domain fragment HsKif15M1P401.

DETAILED DESCRIPTION OF THE INVENTION

I. Definitions

An "agricultural compound" as used herein refers to a chemical or biological compound that has utility in agriculture and functions to foster food or fiber crop protection or yield improvement. For example, one such compound may serve as a herbicide to selectively control weeds, as a fungicide to control the spreading of plant diseases, as an insecticide to ward off and destroy insect and mite pests. In addition, one such compound may demonstrate utility in seed treatment to improve the growth environment of a germinating seed, seedling or young plant as a plant regulator or activator.

"Amplification" primers are oligonucleotides comprising either natural or analogue nucleotides that can serve as the basis for the amplification of a select nucleic acid sequence. They include, e.g., polymerase chain reaction primers and ligase chain reaction oligonucleotides.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The term antibody also includes antibody fragments either produced by the modification of whole antibodies or those synthesized de novo using recombinant DNA methodologies.

An "anti-HsKif15" antibody is an antibody or antibody fragment that specifically binds a polypeptide encoded by the HsKif15 gene, cDNA, or a subsequence thereof.

"Biologically active" HsKif15 refers to HsKif15 that has microtubule stimulated ATPase activity, as tested, e.g., in an ATPase assay, a microtubule gliding, assay, or a microtubule binding assay. "ATPase activity" refers to ability to hydrolyze ATP.

"Biological sample" as used herein is a sample of biological tissue or fluid that contains HsKif15 or a fragment thereof or nucleic acid encoding a HsKif15 protein. Biological samples may also include sections of tissues such as frozen sections taken for histological purposes. A biological sample comprises at least one cell, preferably plant or vertebrate. Embodiments include cells obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

A "comparison window" includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., supra).

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987). The method used is similar to the method described by Higgins & Sharp, CABIOS 5:151–153 (1989). The program can align up to 300 sequences of a maximum length of 5,000. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can be used also to plot a dendogram or tree representation of clustering relationships.

Another example of an algorithm that is suitable for determining percent sequence identity (i.e.., substantial similarity or identity) is the BLAST algorithm, which is described in Altschul et al., J. Mol. Biol. 215:403–410 (1990). Software for performing BLAST analyses is publicly available through the National Center for Biotechnology Information.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, Proteins (1984)).

"Cytoskeletal component" denotes any molecule that is found in association with the cellular cytoskeleton, that plays a role in maintaining or regulating the structural integrity of the cytoskeleton, or that mediates or regulates motile events mediated by the cytoskeleton. Includes cytoskeletal polymers (e.g., actin filaments, microtubules, myosin fragments, filaments), molecular motors, and cytoskeleton associated regulatory proteins (e.g., tropomysoin, alpha-actinin).

"Cytoskeletal function" biological roles of the cytoskeleton: to provide structural organization (e.g., microvilli, mitotic spindle) and to mediate motile events within the cell (e.g., muscle contraction, mitotic contractile ring, pseudopodal movement, active cell surface deformations, vesicle formation and translocation.)

A "diagnostic" as used herein is a compound that assists in the identification and characterization of a health or disease state. The diagnostic can be used in standard assays as is known in the art.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"HsKif15" is a member of the kinesin superfamily of microtubule motor proteins. HsKif15 has activity such as microtubule stimulated ATPase activity and microtubule binding activity.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid.

"High stringency conditions" may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1%

SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"High throughput screening" as used herein refers to an assay which provides for multiple candidate agents or samples to be screened simultaneously. As further described below, examples of such assays may include the use of microtiter plates and nucleic acid or protein arrays which are especially convenient because a large number of assays can be carried out simultaneously, using small amounts of reagents and samples.

By "host cell" is meant a cell that contains an expression vector and supports the replication or expression of the expression vector. Host cells may be prokaryotic cells such as E. cole, or eukaryotic cells such as yeast, insect, amphibian, or mammalian cells such as plant cells, CHO, HeLa and the like. Both primary cells and tissue cultures cells are included in this definition.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. Typically, stringent conditions will be those in which the salt concentration is less than about 1.0 M sodium ion, typically about 0.05 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The terms "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. This definition also refers to the complement of a test sequence, which has a designated percent sequence or subsequence complementarity when the test sequence has a designated or substantial identity to a reference sequence. Preferably, the percent identity exists over a region of the sequence that is at least about 25 amino acids in length, more preferably over a region that is 50 or 100 amino acids in length.

When percentage of sequence identity is used in reference to proteins or peptides, it is recognized that residue positions that are not identical often differ by conservative amino acid substitutions, where amino acid residues are substituted for other amino acid residues with similar chemical properties (e.g,. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. The scoring of conservative substitutions is calculated according to, e.g., the algorithm of Meyers & Millers, Computer Applic. Biol. Sci. 4:11–17 (1988), e.g., as implemented in the program PC/GENE (Intelligenetics, Mountain View, Calif.).

The term "immunoassay" is an assay that uses an antibody to specifically bind an antigen. The immunoassay is characterized by the use of specific binding properties of a particular antibody to isolate, target, and/or quantify the antigen.

The term "in vivo" refers to applications which occur in a cell while in an organism. The term "in vitro" refers to applications which are outside of the organism, and can be in a cell or cell free environment. "In situ" refers to applications which undergo a combination of environments, for example, when a cell is manipulated and then transposed to an organism.

The terms "isolated", "purified", or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In an isolated HsKif15 nucleic acid is separated from open reading frames which flank the HsKif15 gene and encode proteins other than HsKif15. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

A "label" is a composition detectable by spectroscopic, photochemical, biochemical, immunochemical, or chemical means. For example, useful labels include fluorescent proteins such as green, yellow, red or blue fluorescent proteins, $^{32}$P, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:2 can be made detectable, e.g., by incorporating a radio-label into the peptide, and used to detect antibodies specifically reactive with the peptide).

A "labeled nucleic acid probe or oligonucleotide" is one that is bound, either covalently, through a linker, or through ionic, van der Waals, or hydrogen bonds to a label such that the presence of the probe may be detected by detecting the presence of the label bound to the probe.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 μg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

"Modulators," "inhibitors," and "activators of HsKif15" refer to modulatory molecules identified using in vitro and in vivo assays for HsKif15 activity. Such assays include ATPase activity, microtubule gliding, microtubule depolymerizing activity, and binding activity such as microtubule binding activity or binding of the nucleotide analogs. Samples or assays that are treated with a candidate agent at a test and control concentration. The control concentration can be zero. If there is a change in HsKif15 activity between the two concentrations, this change indicates the identification of a modulator. A change in activity, which can be an increase or decrease, is preferably a change of at least 20% to 50%, more preferably by at least 50% to 75%, more preferably at least 75% to 100%, and-more preferably 150% to 200%, and most preferably is a change of at least 2 to 10 fold compared to a control. Additionally, a change can be indicated by a change in binding specificity or substrate.

"Molecular motor" refers to a cytoskeletal molecule that utilizes chemical energy to produce mechanical force, and drives the motile properties of the cytoskeleton.

The phrase "motor domain" refers to the domain of HsKif15 that confers membership in the kinesin superfamily of motor proteins through a sequence identity of approximately 35–45% identity to the motor domain of true kinesin.

The term "nucleic acid" refers to deoxyribonucleotides or ribonucleotides and polymers thereo fin either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutuions may be achieved by generating sequences in which the third position of one or more selected (or all) codons is substituted with mixed-ase and/or deoxyinosine residues (Batzer et al., Nucleic Acid Res. 19:5081 (1991); Ohtsuka et al., J. Biol. Chem. 260)2605–2608 (1985); Cassol et al. 1992; Rossolini et al. Mol. Cell. Probes 8:91–98 (1994)). The term nucleic acid is used interchangeably with gene, cDNA, and mRNA encoded by a gene.

"Nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases. In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled withisotopes, chromophores, lumiphores, chromogens, or indirectly labeled such as with biotin to which a streptavidine complex may later bind. By assaying for the presence or absence of the probe, one can detect the presence or absence of the select sequence or subsequence.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. A HsKif15 polypeptide comprises a polypeptide demonstrated to have at least microtubule stimulated ATPase activity and that binds to an antibody generated against HsKif15. Amino acids may be referred to herein by either their commonly known three letter symbols or by Nomenclature Commission. Nucleotides, likewise, may be referred to by their commonly accepted single-letter codes the one-letter symbols recommended by the IUPAC-IUB Biochemical.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter that is active under most environmental and developmental conditions. An "inducible" promoter is a promoter that is under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, antibodies raised to HsKif15 with the amino acid sequence encoded in SEQ ID NO:2 can be selected to obtain only those antibodies that are specifically immunoreactive with HsKif15 and not with other proteins, except for polymorphic variants, orthologs, alleles, and closely related homologues of HsKif15. This selection may be achieved by subtracting out antibodies that cross react with molecules such as *C. elegans* unc-104 and mammalian Kif1. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind" to a protein, as defined above.

The phrase "a sequence encoding a gene product" refers to a nucleic acid that contains sequence information. This phrase specifically encompasses degenerate codons (i.e., different codons which encode a single amino acid) of the native sequence or sequences which may be introduced to conform with codon preference in a specific host cell.

"Test composition" (used interchangeably herein with "candidate agent" and "test compound" and "test agent") refers to a molecule or composition whose effect on the interaction between two or more cytoskeletal components it is desired to assay. The "test composition" can be any molecule or mixture of molecules, optionally in a A "therapeutic" as used herein refers to a compound which is believed to be capable of modulating the cytoskeletal system in vivo which can have application in both human and animal disease. Modulation of the cytoskeletal system would be desirable in a number of conditions including, but not limited to: abnormal stimulation of endothelial cells (e.g., atherosclerosis), solid and hematopoetic tumors and tumor metastasis, benign tumors, for example, hemangiomas, acoustic neuromas, neurofibromas, pyogenic granulomas, vascular malfunctions, abnormal would healing, inflammatory and immune disorders such as rheumatoid arthritis, Bechet's disease, gout or gouty arthritis, abnormal angiogenesis accompanying: rheumatoid arthritis, psoriasis, diabetic retinopathy, and other ocular angiogenic disesase such as, macular degeneration, corneal graft rejection, corneal overgrowth, glaucoma, Osler Webber syndrome, cardiovascular diseases such as hypertension, cardiac ischemia and systolic and diastolic dysfunction and fungal diseases such as aspergillosis, candidiasis, and topical fungal diseases.

II. Introduction

The present invention provides for the first time a nucleic acid encoding HsKif15. This protein is a member of the kinesin superfamily of motor proteins and demonstrates microtubule stimulated ATPase activity. HsKif15 has been found to be essential for mitotic spindle formation.

In one aspect, HsKif15 can be defined by having at least one or preferably more than one of the following functional and structural characteristics. Functionally, HsKif15 has a microtubule-stimulated ATPase activity, and microtubule motor activity that is ATP dependent. HsKif15 activity can also be described in terms of its binding activity.

The novel nucleotides sequences provided herein encode HsKif15 or fragments thereof. Thus, in one aspect, the nucleic acids provided herein are defined by the novel proteins provided herein. The protein provided herein comprises an amino acid sequence which has one or more of the following characteristics: greater than 70% sequence identity with SEQ ID NO:2, preferably greater than 80%, more preferably greater than 90%, more preferably greater than 95% or, in another embodiment, has 98 to 100% sequence identity with SEQ ID NO:2. As described above, when describing the nucleotide is terms of SEQ ID NO:1, the sequence identity may be slightly lower due to the degeneracy in the genetic code.

The predicted structure of HsKif15 comprises an amino-terminal, kinesin-like microtubule "motor" domain (see FIGS. 4 and 6).

Portions of the HsKif15 nucleotide sequence may be used to identify polymorphic variants, orthologs, alleles, and homologues of HsKif15. This identification can be made in vitro, e.g., under stringent hybridization conditions and sequencing, or by using the sequence information in a computer system for comparison with other nucleotide sequences. Sequence comparison can be performed using any of the sequence comparison algorithms discussed below, with PILEUP as a preferred algorithm.

The activity of any of the peptides provided herein can be routinely confirmed by the assays provided herein such as those which assay ATPase activity or microtubule binding activity. In one embodiment, polymorphic variants, alleles, and orthologs, homologues of HsKif15 are confirmed by using a ATPase or microtubule binding assays as known in the art.

The isolation of biologically active HsKif15 for the first time provides a means for assaying for modulators of this kinesin superfamily protein. Biologically active HsKif15 is useful for identifying modulators of HsKif15 or fragments thereof and kinesin superfamily members using in vitro assays such as microtubule gliding assays, ATPase assays (Kodama et al., *J. Biochem.* 99:1465–1472 (1986); Stewart et al., *Proc. Nat'l Acad. Sci. USA* 90:5209–5213 (1993)), and binding assays including microtubule binding assays (Vale et al., *Cell* 42:39–50 (1985)). In vivo assays and uses are provided herein as well. Also provided herein are methods of identifying candidate agents which bind to HsKif15 and portions thereof.

As further described herein, a wide variety of assays, therapeutic and diagnostic methods are provided herein which utilize the novel compounds described herein. The uses and methods provided herein, as further described below have in vivo, in situ, and in vitro applications, and can be used in medicinal, veterinary, agricultural and research based applications.

III. Isolation of the Gene Encoding HsKif15

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from mass spectroscopy, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.* 12:6159–6168 (1984). Purification of oligonculeotides is by either native acrylamide gel electrophoresis or by anion-exchange HPLC as described in Pearson & Reanier, *J. Chrom.* 225:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding HsKif15

In general, the nucleic acid sequences encoding HsKif15 and related nucleic acid sequence homologs are cloned from cDNA and genomic DNA libraries or isolated using amplification techniques with oligonucleotide primers. Alternatively, expression libraries can be used to clone HsKif15 and HsKif15 homologues by detected expressed homologues immunologically with antisera or purified antibodies made against HsKif15 that also recognize and selectively bind to the HsKif15 homologue. Finally, amplification techniques using primers can be used to amplify and isolate HsKif15 from DNA or RNA. Amplification techniques using degenerate primers can also be used to amplify and isolate HsKif15 homologues. Amplification techniques using primers can also be used to isolate a nucleic acid encoding HsKif15. These primers can be used, e.g., to amplify a probe of several hundred nucleotides, which is then used to screen a library for full-length HsKif15.

Appropriate primers and probes for identifying the gene encoding HsKif15 in other species are generated from comparisons of the sequences provided herein. As described above, antibodies can be used to identified HsKif15 homologues. For example, antibodies made to the motor domain of HsKif15 or to the whole protein are useful for identifying HsKif15 homlogues.

To make a cDNA library, one should choose a source that is rich in the mRNA of choice, e.g., HsKif15. For example, HsKif15 mRNA is most abundant in testes, bone marrow and in fetal liver, with relatively lower levels of expression in brain, salivary gland, heart, thyroid, kidney, adrenal gland, spleen, pancreas, liver, ovary, colon, uterus, lung, prostate, small intestine, skin, muscle, peripheral blood lymphocytes, stomach, and placenta. The mRNA is then made into cDNA using reverse transcriptase, ligated into a recombinant vector, and introduced into a recombinant host for propagation, screening and cloning. Methods for making and screening cDNA libraries are well known (see, e.g., Gubler & Hoffman, Gene 25: 263–269); Sambrook et al., supra; Ausubel et al., supra).

For a genomic library, the DNA is extracted from the tissue and either mechanically sehared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, Science 196:180–182 (1977). Colony hybridization is arre dout as generally described in Grunstein et al., Proc. Natl. Acad. Sci. USA, 72:3961–3965 (1975).

An alternative method of isolating HsKif15 nucleic acid and its homologues combines the use of synthetic oligonucleotide primers and amplification of an RNA or DNA template (see U.S. Pat. Nos. 4,683,195 and 4,683,202; PCR Protocols: A guide to Methods and Applications (Innis et al., eds. 1990)). Methods such as polymerase chain reaction and ligase chain reaction can be used to amplify nucleic acid sequences of HsKif15 directly from mRNA, from cDNA, from genomic libraries or cDNA libraries.

Degenerate oligonucleotides can be designed to amplify HsKif15 homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of HsKif15 encoding mRNA in physiological samples, for nucleic sequencing or for other purposes. Genesamplified by the PCR reaction can be purified from agarose gels and cloned into an appropriate vector.

Gene expression of HsKif15 can also be analyzed by techniques known in the art, e.g., reverse transcription and amplification of mRNA, isolation of total RNA or poly A+RNA, northern blotting, dot blotting, in situ hybridization, Rnase protection, quantitative PCR, and the like.

Synthetic oligonucleotides can be used to construct recombinant HsKif15 genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the HsKif15 gene. The specific subsequence is then ligated into an expression vector.

The gene for HsKif15 is typically cloned into intermediate vectors before transformation into prokaryotic or eukaryotic cells for replication and/or expression. The intermediate vectors are typically prokaryote vectors or shuttle vectors.

C. Expession in Prokaryotes and Eukaryotes

To obtain high level expression of a cloned gene, such as those cDNAs encoding HsKif15, it is important to construct an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the HsKif15 protein are available in, e.g., *E. coli, Bacillus sp.,* and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. The pET expression system (Novagen) is a preferred prokaryotic expression system.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the HsKif15 encoding nucleic acid in host cells. A typical expression cassette thus contains a promoter operably linked to the nucleic acid sequence encoding HsKif15 and signals required for efficient polyadenylation of the transcript, ribosome binding sites, and translation termination. The nucleic acid sequence encoding HsKif15 may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, cytomegalovirus vectors, papilloma virus vectors, and vectors derived from Epstein Bar virus. Other exemplary eukaryotic vectors include pMSG, pAV009/A+, pMTO10/A−, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a HsKif15 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection or transformation methods are used to produce bacterial, mammalian, yeast or insect cell lines that express large quantities of HsKif15 protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher ed., 1990)).

Transformation of eukaryotic and prokaryotic cells are performed according to standard techniques (see, e.g., Morrison, *J. Bact.*, 132:349–351 (1977); Clark-Curtiss & Curtiss, *Methods in Enzymology*, 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing HsKif15.

After the expression vector is introduced into the cells, the transfected cells are cultured under conditions favoring expression of HsKif15, which is recovered from the culture using standard techniques identified below.

IV. Purification of HsKif15 Protein

Either naturally occurring or recombinant HisKif 15 can be purified for use in functional assays. HsKif15 may be purified to substantial purity by standard techniques, including selective precipitation with such substances as ammnonium sulfate; column chromatography, immunopurification methods, and others (see, e.g., Scopes, Protein Purification: Principles and Practice (1982); U.S. Pat. No. 4,673,641; Ausubel et al. supra; and Sambrook et al., supra). A preferred method of purification is use of Ni-NTA agarose (Qiagen).

A number of procedures can be employed when recombinant HsKif15 is being purified. For example, proteins having established molecular adhesion properties can be reversibly fused to HsKif15. With the appropriate ligand, HsKif15 can be selected adsorbed to a purification column and then freed from the column in a relatively pure form. The fused protein is then removed by enzymatic activity. Finally, HsKif15 could be purified using immunoaffinity columns.

A. Purification of UsKif15 From Recombinant Bacteria

Recombinant proteins are expressed by transformed bacteria in large amounts, typically after promoter induction; but expression can be constitutive. Promoter induction with IPTG is a preferred method of expression. Bacteria are grown according to standard procedures in the art. Fresh or frozen bacteria cells are used for isolation of protein.

Alternatively, it is possible to purify HsKif15 from bacteria periplasm. After lysis of the bacteria, when HsKif15 is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

HsKif15 or fragments thereof can also be prepared according to the procedures set forth in U.S. patent application No. 09/295,612, which is incorporated herein for all purposes.

B. Standard Protein Separation Techniques For Purifying HsKif15 Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of HsKif15 can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

HsKif15 can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of HsKif15

In addition to the detection of HsKif15 genes and gene expression using nucleic acid hybridization technology, one can also use immunoassays to detect HsKif15. Immunoassays can be used to qualitatively or quantitatively analyze HsKif15. A general overview of the applicable technology can be found in Harlow & Lane, *Antibodies: A Laboratory Manual* (1988).

A. Antibodies to HsKif15

Methods of producing polyclonal and monoclonal antibodies that react specifically with HsKif15 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of HsKif15 comprising immunogens may be used to produce antibodies specifically reactive with HsKif15. For example, recombinant HsKif15 or a antigenic fragment thereof such as the motor domain, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to HsKif15. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-HsKif15 proteins or even other homologous proteins from other organisms (e.g., *C. elegans* unc-104 or mammalian Kif1), using a competitive binding immunoassay. Specific polyclonal antisera and monoclonal antibodies will usually bind with a $K_D$ of at least about 0.1 mM, more usually at least about 1 ìM, preferably at least about 0. 1 ìM or better, and most preferably, 0.01 ìM or better.

Once HsKif15 specific antibodies are available, HsKif15 can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio ed., 1980); and Harlow & Lane, supra.

B. Binding Assays

Antibodies can be used for treatment or to identify the presence of HsKif15 having the sequence identity characteristics as described herein. Additionally, antibodies can be used to identify modulators of the interaction between the antibody and HsKif15 as further described below. While the following discussion is directed toward the use of antibodies in the use of binding assays, it is understood that the same general assay formats such as those described for "non-competitive" or "competitive" assays can be used with any compound which binds to HsKif15 such as microtubules or the compounds described in Serial No. 60/070,772.

In a preferred embodiment, HsKif15 is detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology* Volume 37: *Antibodies in Cell Biology* (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the HsKif15 or antigenic subsequence thereof). The antibody (e.g., anti-HsKif15) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled HsKif15 polypeptide or a labeled anti-HsKif15 antibody. Alternatively, the labeling agent may be a third moiety, such a secondary antibody, that specifically binds to the antibody/ HsKif15 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see generally Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting HsKif15 in samples may be either competitive or noncompetitive. Noncompetitive immunoassays are assays in which the amount of antigen is directly measured. In one preferred "sandwich" assay, for example, the anti-HsKif15 antibodies can be bound directly to a solid substrate on which they are immobilized. These immobilized antibodies then capture HsKif15 present in the test sample. HsKif15 is thus immobilized is then bound by a labeling agent, such as a second HsKif15 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of HsKif15 present in the sample is measured indirectly by measuring the amount of a known, added (exogenous) HsKif15 displaced (competed away) from an anti-HsKif15 antibody by the unknown HsKif15 present in a sample. In one competitive assay, a known amount of HsKif15 is added to a sample and the sample is then contacted with an antibody that specifically binds to HsKif15. The amount of exogenous HsKif15 bound to the antibody is inversely proportional to the concentration of HsKif15 present in the sample. In a particularly preferred embodiment, the antibody is immobilized on a solid substrate. The amount of HsKif15 bound to the antibody may be determined either by measuring the amount of HsKif15 present in a HsKif15/antibody complex, or alternatively by measuring the amount of remaining uncomplexed protein. The amount of HsKif15 may be detected by providing a labeled HsKif15 molecule.

A hapten inhibition assay is another preferred competitive assay. In this assay the known HsKif15, is immobilized on a solid substrate. A known amount of anti-HsKif15 antibody is added to the sample, and the sample is then contacted with the immobilized HsKif15. The amount of anti-HsKif15 antibody bound to the known immobilized HsKif15 is inversely proportional to the amount of HsKif15 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations. For example, a protein at least partially encoded by SEQ ID NO:2 can be immobilized to a solid support. Proteins (e.g., *C. elegans* unc-104 or mammalian Kif1) are added to the assay that compete for binding of the antisera to the immobilized antigen. The ability of the added proteins to compete for binding of the antisera to the immobilized protein is compared to the ability of HIsKif15 encoded by SEQ ID NO:2 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologues.

The immunoabsorbed and pooled antisera are then used in a competitive binding immunoassay as described above to compare a second protein, thought to be perhaps the protein of this invention, to the immunogen protein (i.e., HsKif15 of SEQ ID NO:2). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2 that is required to inhibit 50% of binding, then the second protein is said to specifically bind to the polyclonal antibodies generated to a HsKif15 immunogen.

Other Assay Formats

Western blot (immunoblot) analysis is used to detect and quantify the presence of HsKif15 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind HsKif15. The anti-HsKif15 antibodies specifically bind to the HsKif15 on the solid support. These antibodies may be directly labeled or alternatively may be subsequently detected using labeled antibodies (e.g., labeled sheep anti-mouse antibodies) that specifically bind to the anti-HsKif15 antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize HsKif15, or secondary antibodies that recognize anti-HsKif15.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of HsKif15

The activity of HsKif15 can be assessed using a variety of in vitro or in vivo assays, e.g, microtubule gliding assays, binding assays such as microtubule binding assays, microtubule depolymerization assays, and ATPase assays (Kodama et al., *J. Biochem.* 99: 1465–1472 (1986); Stewart et al., *Proc. Nat'l Acad. Sci. USA* 90: 5209–5213 (1993); (Lombillo et al, *J. Cell Biol.* 128:107–115 (1995); (Vale et al., Cell 42:39–50 (1985)). A preferred assay for high throughput screening is an ATPase assay with colorimetric detection, e.g., malachite green for end-point detection or coupled PK/LDH for continuous rate monitoring.

Such assays can be used to test for the activity of HsKif15 isolated from endogenous sources or recombinant sources. Furthermore, such assays can be used to test for modulators of HsKif15.

Modulators of HsKif15 activity are tested using biologically active HsKif15. Modulation is tested using one of the in vitro or in vivo assays known in the art, e.g., ATPase, microtubule gliding, and microtubule binding.

In a preferred embodiment, molecular motor activity is measured by the methods disclosed in Ser. No. 09/314,464, filed May 18, 1999, entitled "Compositions and assay utilizing ADP or phosphate for detecting protein modulators", which is incorporated herein by reference in its entirety. More specifically, this assay detects modulators of any aspect of a kinesin motor function ranging from interaction with microtubules to hydrolysis of ATP. ADP or phosphate is used as the readout for protein activity.

In specific embodiments, screens may be designed to first find candidate agents that can bind to HsKif15 proteins, and then these agents, and agents already known to modulate HsKif15 may be used in assays that evaluate the ability of the candidate agent to modulate activity of HsKif15. Thus, as will be appreciated by those in the art, there are a number of different assays which may be run; binding assays and activity assays.

Thus, in a preferred embodiment, the methods comprise combining a HsKif15 protein and a candidate agent, and determining the binding of the candidate agent to the HsKif15 protein. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. In a preferred embodiment, the candidate agents are organic chemical moieties, a wide variety of which are available in the literature.

The assays provided utilize HsKif15 proteins as defined herein. In one embodiment, portions of HsKif15 proteins are utilized; in a preferred embodiment, portions having HsKif15 activity as described herein are used. In addition, the assays described herein may utilize either isolated HsKif15 proteins or cells or animal models comprising the HsKif15 proteins.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

VII. Diagnostic Assays and Kits

As described above, HsKif15 and its homologues are also a useful diagnostic tool in vitro. Such assays use HsKif15 specific reagents that specifically hybridize to HsKif15 nucleic acid, such as HsKif15 probes and primers, and HsKif15 specific reagents that specifically bind to the HsKif15 protein, e.g., HsKif15 antibodies.

Nucleic acid assays for the presence of HsKif15 DNA and RNA in a sample are useful diagnostic assays. Numerous techniques are known to those skilled in the art, including Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al, *Methods in Virology*, vol. VII, pp. 189–226 (1984); and *Nucleic Acid Hybridization: A Practical Approach* (Hames et al., eds. 1987). In addition, HsKif15 protein can be detected with the various immunoassay techniques described above. The test sample is typically compared to both a positive control (e.g, a sample expressing recombinant HsKif15) and a negative control (e.g., a negative sample from Saccharomyces).

The present invention also provides for kits for screening for modulators of HsKif15. Such kits can be prepared from readily available materials and reagents. For example, such kits can comprise any one or more of the following materials: biologically active HsKif15, reaction tubes, and instructions for testing HsKif15 activity. Preferably, the kit contains biologically active HsKif15. A wide variety of kits and components can be prepared according to the present invention, depending upon the intended user of the kit and the particular needs of the user. For example, the kit can be tailored for ATPase assays, microtubule gliding assays, or microtubule binding assays.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety.

What is claimed is:

1. A method for screening for modulators of a target protein, wherein the target protein has microtubule stimulated ATPase activity and comprises a sequence that has greater than 90% amino acid sequence identity to SEQ ID NO:2, SEQ ID NO:4, or SEQ ID NO:6 as measured using a sequence comparison algorithm, the method comprising the steps of:

contacting the target protein with a candidate agent at a first concentration and determining a level of activity of the target protein; and contacting the target protein with a candidate agent at a second concentration; and determining a level of activity of the target protein; wherein the activity is selected from the group consisting of binding activity or ATPase activity, and wherein a difference between the level of activity of the target protein contacted with the first concentration of the candidate agent and the level of activity of the target protein contacted with the second concentration of the candidate agent indicates that the candidate agent modulates the activity of the target protein.

2. A method of claim 1, wherein the screening occurs in a multi-well plate a part of a high-throughput screen.

3. A method of claim 1, wherein the target protein comprises an amino acid sequence of SEQ ID NO:2, SEQ ID NO:4 or SEQ ID NO:6.

4. A method of claim 1, wherein the target protein has greater than 95% amino acid sequence identity to SEQ ID NO:2, SEQ ID NO:4, or SEQ ID NO:6 as measured using a sequence comparison algorithm.

5. A method of claim 1, wherein the target protein has greater than 98% amino acid sequence identity to SEQ ID NO:2, SEQ ID NO:4, or SEQ ID NO:6 as measured using a sequence comparison algorithm.

6. A method of claim 1, wherein the target protein has been isolated from an endogenous source.

7. A method of claim 1, wherein the target protein has been produced recombinantly.

8. A method of claim 1, wherein said first concentration or said second concentration of the candidate agent is zero or a level below detection.

9. A method of claim 1, wherein the candidate agent is an agonist.

10. A method of claim 1, wherein the candidate agent is an antagonist.

11. A method of claim 1, wherein the candidate agent binds to the target protein.

12. A method of claim 1, wherein the target protein is contacted with the candidate agent in vivo.

13. A method of claim 1, wherein the target protein is contacted with the candidate agent in vitro.

14. A method of claim 1, wherein contacting the target protein with a candidate agent comprises adding the candidate agent to a mixture comprising the target protein under conditions which normally allow the production of ADP or phosphate.

15. A method of claim 14, wherein determining the level of activity of the target protein comprises the steps of:

i) subjecting the mixture to an enzymatic reaction, wherein said enzymatic reaction uses ADP or phosphate as a substrate under conditions which normally allow the ADP or phosphate to be utilized; and ii) measuring NADH consumption as a measure of ADP production, wherein a change in measure of NADH consumption between the first and second concentrations of the candidate agent indicates that the candidate agent is a modulator of the target protein.

16. A method of claim 1, wherein the candidate agent is labeled.

* * * * *

SEQUENCE LISTING

<160> NUMBER OF SEQ ID NOS: 6

<210> SEQ ID NO 1
<211> LENGTH: 4757
<212> TYPE: DNA
<213> ORGANISM: Human

<400> SEQUENCE: 1

```
atggcacccg gctgcaaaac tgagttacgc agcgtgacaa atggtcagtc taaccaacca      60
agtaatgaag gtgatgccat caaagttttt gtgcgaattc gtcctcctgc agaaagatct     120
gggtcagctg atggagagca gaacttatgc ttatctgtgc tgtcctccac gagtctccgg     180
ctgcactcca accctgagcc caagaccttc acgtttgatc atgttgcaga tgtggatacc     240
actcaggaat ctgtattcgc aactgtggct aaaagcattg tggagtcttg catgagcggt     300
tataatggta ccatctttgc atatggacag actggctcag ggaagacatt tactatgatg     360
ggaccatctg aatctgataa ttttctcat aacctgagag gagtaatccc acgaagtttt      420
gaatatttgt tttccttaat tgatcgtgaa aagaaaagg ctggagctgg aaagagtttc     480
ctttgtaagt gttcctttat tgaaatctac aacgagcaga tatatgatct actggactct     540
gcatcggctg gactgtactt aagggagcat atcaagaagg gagtctttgt tgttggtgcg     600
```

-continued

| | |
|---|---|
| gtggagcagg tggtaacctc agctgctgaa gcctatcagg tgttgtctgg aggatggagg | 660 |
| aatagacgtg tggcatcaac atcaatgaac agagaatcgt ctaggtctca tgccgtcttt | 720 |
| acaattacaa tagagtcaat ggagaaaagt aatgagattg tgaatatacg gacctcccta | 780 |
| ctcaacctgg tggatttagc aggatctgaa aggcaaaaag atacccatgc agaagggatg | 840 |
| agattgaagg aagcaggtaa cataaatcga tcattgagct gcctgggcca agtgattaca | 900 |
| gcacttgtcg acgtgggtaa tggaaaacag agacatgttt gctacagaga ctccaaactt | 960 |
| accttcttac tacgggattc ccttggaggt aatgccaaaa cagccataat tgcaaatgtt | 1020 |
| catcctggat ccaggtgttt tggggaaacc ctatcaacac ttaactttgc tcaaagagcc | 1080 |
| aagctgatta aaacaaggc agtagtaaat aagacaccc aaggaaatgt gagccagctc | 1140 |
| caagctgaag tgaagaggct caaagaacaa ctggcggagc ttgcttcagg acagacacca | 1200 |
| ccagaaagct tcctgaccag agacaaaaag aagactaact atatggagta tttccaggaa | 1260 |
| gcaatgttat tctttaagaa atctgaacag gaaagaagt ctctgataga aaagttacc | 1320 |
| caattagaag acctcaccct caaaaaggaa aaatttattc aatctaataa aatgattgtg | 1380 |
| aaattccgag aggatcaaat aatacgcttg gaaaagctcc acaaggaatc ccggggaggt | 1440 |
| tttctgcctg aggagcagga tcgtttgctc tcagaattaa ggaatgagat tcaaactctg | 1500 |
| cgagaacaaa tagagcacca ccccagagtt gcaaagtatg ctatggaaaa tcattccctc | 1560 |
| agggaggaga atagaagact gagattatta gagcctgtga aaagagctca agaaatggat | 1620 |
| gcccagacca ttgcaaaact agaaaaagct ttctctgaaa taagtggcat ggagaaaagt | 1680 |
| gacaaaaatc agcaaggatt ttcacctaaa gctcagaaag agccatgttt gtttgcaaac | 1740 |
| actgagaagt taaaagcaca actcctgcaa attcagacag agctgaataa ttcaaagcaa | 1800 |
| gaatatgaag aattcaaaga acttactagg aaaaggcagc tagaattgga atcagagctt | 1860 |
| cagtctttgc aaaaagcgaa ccttaatctt gaaaacctt tggaagcaac aaaagcctgc | 1920 |
| aagcggcaag aagtttctca gctgaataaa attcatgctg aaacacttaa gattataact | 1980 |
| acaccaacca aggcctacca acttcattcc cgaccagtac caaaattaag ccctgaaatg | 2040 |
| ggaagctttg gctctctata cactcagaat tctagcatat tagataatga tatattaaat | 2100 |
| gagccagttc ctcctgagat gaatgaacaa gcttttgagg ccatttctga agagcttaga | 2160 |
| acagtgcagg aacaaatgag tgctcttcaa gccaaactgg atgaagaaga gcataaaaac | 2220 |
| ctaaagcttc agcagcatgt tgacaaactg gaacatcatt ctacccaaat gcaggagctt | 2280 |
| ttctcatcag aaagaattga ttggaccaaa cagcaggaag agcttctctc acagttgaat | 2340 |
| gtccttgaaa agcagcttca agagactcaa actaaaaatg acttttttgaa aagtgaggta | 2400 |
| catgacctgc gagtagtcct tcattctgct gacaaggagc tttcttcagt gaaattggaa | 2460 |
| tatagttcat tcaaaacgaa tcaggagaaa gaattcaaca aactttccga agacacatg | 2520 |
| catgtacagc ttcaattaga taatctcagg ttagaaaacg aaaagctgct tgagagcaaa | 2580 |
| gcctgcctac aggattccta tgacaactta caagaaataa tgaaatttga gattgaccaa | 2640 |
| cttttcaagaa acctccaaaa cttcaaaaaa gaaaatgaaa ctctgaaatc tgatctgaat | 2700 |
| aatttgatgg agcttcttga ggcagaaaaa gaacgcaata acaaattatc attacagttt | 2760 |
| gaagaagata agaaaacag ttctaaagaa atcttaaaag ttcttgaggc tgtacgtcag | 2820 |
| gagaaacaga aagagacggc caagtgtgag cagcagatgg caaaagtaca gaaactagaa | 2880 |
| gagagcttgc ttgctactga aaaagtgatc agttccctgg aaaagtctag agattctgat | 2940 |
| aagaaagttg tagctgacct catgaaccag atccaggagc taagatcatc ggtctgtgag | 3000 |

-continued

```
aaaacagaaa ctatagacac cctgaaacaa gaactgaagg acataaattg caaatacaac    3060
tctgctttgg ttgacagaga agagagcaga gtgttgatca agaagcagga agtggatatt    3120
ctggatctga agaaacccct taggctgaga atactttctg aggacataga gagggatatg    3180
ctctgtgagg acctggctca tgccactgag cagctgaaca tgctcacaga ggcctcaaaa    3240
aaacactcgg ggctgctgca gtctgcccag gaagaactga ccaagaagga agccctgatt    3300
caggaacttc agcacaagct aaaccaaaag aaagaggaag tagaacagaa gaagaatgaa    3360
tataacttca aaatgaggca actagaacat gtgatggatt ctgctgctga ggatccccag    3420
agtcctaaga caccacctca ctttcaaaca catttggcaa aactcctgga acacaagaa    3480 caagagatag aagatggaag agcctctaag acttctttgg aacaccttgt aacaaagcta    3540
aatgaagaca gagaagtcaa aaatgctgaa atcctcagaa tgaaggagca gttgcgtgaa    3600
atggaaaacc tacgcctgga aagtcagcag ttaatagaga aaaactggct cctgcaaggt    3660
cagctggatg atattaaaag acaaaaggaa aacagtgatc agaatcatcc agataatcaa    3720
cagctgaaga atgaacaaga agaaagtatc aagaaaagac ttgcaaaaag taaaatagtt    3780
gaagaaatgc tgaaaatgaa agcagaccta aagaagtcc aaagtgccct ttacaacaaa    3840
gagatggaat gccttagaat gactgatgaa gtcgaacgaa cccaaacttt ggagtctaaa    3900
gcattccagg aaaagaaaca actgagatca aagctggaag aaatgtatga agaaagagag    3960
agaacatccc aggagatgga aatgttaagg aagcaggtgg agtgtcttgc tgaggaaaat    4020
ggaaagttgg taggtcacca aaatttgcat cagaagattc agtacgtagt gcgactaaag    4080
aaggaaaatg tcaggcttgc tgaggagaca gaaaagttgc gtgccgaaaa tgtatttta    4140 aaagaaaaga aagaagtgaa atcttgagga ttccggtcag ctacctaggc atcaccttgt    4200
ttgaagatgt tcttctctt ttacaagtaa gacctactcc tggccactta ggagagctga    4260
atttatggac cttaattatt aaatgtttat aaggtggtgg taaccacctc aagtttctga    4320
tgaacattct gcatccatat acaccctgtg acagtcagca gtctgctatt aagtggccta    4380
cttcaaggct ttgaatcaac ttaagggaaa accttttgtc tttgtaaaaa taaaagcctg    4440
tagctaaggt ttacagtgga cattagccag atcattttct tcttagatta tgccataatc    4500
tcctttgatt cttatggaag ttctaacaat atatggtggt tccaacacct gcagtgagtt    4560
taatgactga cttagtagca ggtacaagaa gcaaacttgt taatatagat tatttttgta    4620
ttcttacttt aggtatttc ttgagcattt tccatgactg taaataaagc catttttaa     4680 gataataaaa aaaaaaaaaa aaaactcgag gggggcccg gtacccaatt cgccctatag    4740
tgagtcgtat tacaatc                                                  4757
```

<210> SEQ ID NO 2
<211> LENGTH: 1388
<212> TYPE: PRT
<213> ORGANISM: Human

<400> SEQUENCE: 2

```
Met Ala Pro Gly Cys Lys Thr Glu Leu Arg Ser Val Thr Asn Gly Gln
 1               5                  10                  15

Ser Asn Gln Pro Ser Asn Glu Gly Asp Ala Ile Lys Val Phe Val Arg
            20                  25                  30

Ile Arg Pro Pro Ala Glu Arg Ser Gly Ser Ala Asp Gly Glu Gln Asn
        35                  40                  45

Leu Cys Leu Ser Val Leu Ser Ser Thr Ser Leu Arg Leu His Ser Asn
```

```
            50                  55                  60
Pro Glu Pro Lys Thr Phe Thr Phe Asp His Val Ala Asp Val Asp Thr
65                  70                  75                  80

Thr Gln Glu Ser Val Phe Ala Thr Val Ala Lys Ser Ile Val Glu Ser
                85                  90                  95

Cys Met Ser Gly Tyr Asn Gly Thr Ile Phe Ala Tyr Gly Gln Thr Gly
            100                 105                 110

Ser Gly Lys Thr Phe Thr Met Met Gly Pro Ser Glu Ser Asp Asn Phe
            115                 120                 125

Ser His Asn Leu Arg Gly Val Ile Pro Arg Ser Phe Glu Tyr Leu Phe
            130                 135                 140

Ser Leu Ile Asp Arg Glu Lys Glu Lys Ala Gly Ala Gly Lys Ser Phe
145                 150                 155                 160

Leu Cys Lys Cys Ser Phe Ile Glu Ile Tyr Asn Glu Gln Ile Tyr Asp
                165                 170                 175

Leu Leu Asp Ser Ala Ser Ala Gly Leu Tyr Leu Arg Glu His Ile Lys
                180                 185                 190

Lys Gly Val Phe Val Val Gly Ala Val Glu Gln Val Val Thr Ser Ala
            195                 200                 205

Ala Glu Ala Tyr Gln Val Leu Ser Gly Gly Trp Arg Asn Arg Arg Val
210                 215                 220

Ala Ser Thr Ser Met Asn Arg Glu Ser Ser Arg Ser His Ala Val Phe
225                 230                 235                 240

Thr Ile Thr Ile Glu Ser Met Glu Lys Ser Asn Glu Ile Val Asn Ile
                245                 250                 255

Arg Thr Ser Leu Leu Asn Leu Val Asp Leu Ala Gly Ser Glu Arg Gln
            260                 265                 270

Lys Asp Thr His Ala Glu Gly Met Arg Leu Lys Glu Ala Gly Asn Ile
            275                 280                 285

Asn Arg Ser Leu Ser Cys Leu Gly Gln Val Ile Thr Ala Leu Val Asp
            290                 295                 300

Val Gly Asn Gly Lys Gln Arg His Val Cys Tyr Arg Asp Ser Lys Leu
305                 310                 315                 320

Thr Phe Leu Leu Arg Asp Ser Leu Gly Gly Asn Ala Lys Thr Ala Ile
            325                 330                 335

Ile Ala Asn Val His Pro Gly Ser Arg Cys Phe Gly Glu Thr Leu Ser
            340                 345                 350

Thr Leu Asn Phe Ala Gln Arg Ala Lys Leu Ile Lys Asn Lys Ala Val
            355                 360                 365

Val Asn Glu Asp Thr Gln Gly Asn Val Ser Gln Leu Gln Ala Glu Val
            370                 375                 380

Lys Arg Leu Lys Glu Gln Leu Ala Glu Leu Ala Ser Gly Gln Thr Pro
385                 390                 395                 400

Pro Glu Ser Phe Leu Thr Arg Asp Lys Lys Thr Asn Tyr Met Glu
                405                 410                 415

Tyr Phe Gln Glu Ala Met Leu Phe Phe Lys Lys Ser Glu Gln Glu Lys
            420                 425                 430

Lys Ser Leu Ile Glu Lys Val Thr Gln Leu Glu Asp Leu Thr Leu Lys
            435                 440                 445

Lys Glu Lys Phe Ile Gln Ser Asn Lys Met Ile Val Lys Phe Arg Glu
            450                 455                 460

Asp Gln Ile Ile Arg Leu Glu Lys Leu His Lys Glu Ser Arg Gly Gly
465                 470                 475                 480
```

```
Phe Leu Pro Glu Glu Gln Asp Arg Leu Leu Ser Glu Leu Arg Asn Glu
            485                 490                 495
Ile Gln Thr Leu Arg Glu Gln Ile Glu His His Pro Arg Val Ala Lys
            500                 505                 510
Tyr Ala Met Glu Asn His Ser Leu Arg Glu Glu Asn Arg Arg Leu Arg
            515                 520                 525
Leu Leu Glu Pro Val Lys Arg Ala Gln Glu Met Asp Ala Gln Thr Ile
        530                 535                 540
Ala Lys Leu Glu Lys Ala Phe Ser Glu Ile Ser Gly Met Glu Lys Ser
545                 550                 555                 560
Asp Lys Asn Gln Gln Gly Phe Ser Pro Lys Ala Gln Lys Glu Pro Cys
                565                 570                 575
Leu Phe Ala Asn Thr Glu Lys Leu Lys Ala Gln Leu Leu Gln Ile Gln
            580                 585                 590
Thr Glu Leu Asn Asn Ser Lys Gln Glu Tyr Glu Glu Phe Lys Glu Leu
        595                 600                 605
Thr Arg Lys Arg Gln Leu Glu Leu Glu Ser Glu Leu Gln Ser Leu Gln
        610                 615                 620
Lys Ala Asn Leu Asn Leu Glu Asn Leu Leu Glu Ala Thr Lys Ala Cys
625                 630                 635                 640
Lys Arg Gln Glu Val Ser Gln Leu Asn Lys Ile His Ala Glu Thr Leu
                645                 650                 655
Lys Ile Ile Thr Thr Pro Thr Lys Ala Tyr Gln Leu His Ser Arg Pro
                660                 665                 670
Val Pro Lys Leu Ser Pro Glu Met Gly Ser Phe Gly Ser Leu Tyr Thr
        675                 680                 685
Gln Asn Ser Ser Ile Leu Asp Asn Asp Ile Leu Asn Glu Pro Val Pro
        690                 695                 700
Pro Glu Met Asn Glu Gln Ala Phe Glu Ala Ile Ser Glu Glu Leu Arg
705                 710                 715                 720
Thr Val Gln Glu Gln Met Ser Ala Leu Gln Ala Lys Leu Asp Glu Glu
                725                 730                 735
Glu His Lys Asn Leu Lys Leu Gln Gln His Val Asp Lys Leu Glu His
            740                 745                 750
His Ser Thr Gln Met Gln Glu Leu Phe Ser Ser Glu Arg Ile Asp Trp
        755                 760                 765
Thr Lys Gln Gln Glu Glu Leu Leu Ser Gln Leu Asn Val Leu Glu Lys
        770                 775                 780
Gln Leu Gln Glu Thr Gln Thr Lys Asn Asp Phe Leu Lys Ser Glu Val
785                 790                 795                 800
His Asp Leu Arg Val Val Leu His Ser Ala Asp Lys Glu Leu Ser Ser
            805                 810                 815
Val Lys Leu Glu Tyr Ser Ser Phe Lys Thr Asn Gln Glu Lys Glu Phe
        820                 825                 830
Asn Lys Leu Ser Glu Arg His Met His Val Gln Leu Gln Leu Asp Asn
            835                 840                 845
Leu Arg Leu Glu Asn Glu Lys Leu Leu Glu Ser Lys Ala Cys Leu Gln
        850                 855                 860
Asp Ser Tyr Asp Asn Leu Gln Glu Ile Met Lys Phe Glu Ile Asp Gln
865                 870                 875                 880
Leu Ser Arg Asn Leu Gln Asn Phe Lys Lys Glu Asn Glu Thr Leu Lys
            885                 890                 895
```

```
Ser Asp Leu Asn Asn Leu Met Glu Leu Leu Glu Ala Glu Lys Glu Arg
            900                 905                 910
Asn Asn Lys Leu Ser Leu Gln Phe Glu Glu Asp Lys Glu Asn Ser Ser
        915                 920                 925
Lys Glu Ile Leu Lys Val Leu Glu Ala Val Arg Gln Glu Lys Gln Lys
    930                 935                 940
Glu Thr Ala Lys Cys Glu Gln Gln Met Ala Lys Val Gln Lys Leu Glu
945                 950                 955                 960
Glu Ser Leu Leu Ala Thr Glu Lys Val Ile Ser Ser Leu Glu Lys Ser
                965                 970                 975
Arg Asp Ser Asp Lys Lys Val Val Ala Asp Leu Met Asn Gln Ile Gln
            980                 985                 990
Glu Leu Arg Ser Ser Val Cys Glu Lys Thr Glu Thr Ile Asp Thr Leu
        995                 1000                1005
Lys Gln Glu Leu Lys Asp Ile Asn Cys Lys Tyr Asn Ser Ala Leu Val
    1010                1015                1020
Asp Arg Glu Glu Ser Arg Val Leu Ile Lys Lys Gln Glu Val Asp Ile
1025                1030                1035                1040
Leu Asp Leu Lys Glu Thr Leu Arg Leu Arg Ile Leu Ser Glu Asp Ile
                1045                1050                1055
Glu Arg Asp Met Leu Cys Glu Asp Leu Ala His Ala Thr Glu Gln Leu
            1060                1065                1070
Asn Met Leu Thr Glu Ala Ser Lys Lys His Ser Gly Leu Leu Gln Ser
        1075                1080                1085
Ala Gln Glu Glu Leu Thr Lys Lys Glu Ala Leu Ile Gln Glu Leu Gln
    1090                1095                1100
His Lys Leu Asn Gln Lys Lys Glu Val Glu Gln Lys Lys Asn Glu
1105                1110                1115                1120
Tyr Asn Phe Lys Met Arg Gln Leu Glu His Val Met Asp Ser Ala Ala
                1125                1130                1135
Glu Asp Pro Gln Ser Pro Lys Thr Pro Pro His Phe Gln Thr His Leu
            1140                1145                1150
Ala Lys Leu Leu Glu Thr Gln Glu Gln Glu Ile Glu Asp Gly Arg Ala
        1155                1160                1165
Ser Lys Thr Ser Leu Glu His Leu Val Thr Lys Leu Asn Glu Asp Arg
    1170                1175                1180
Glu Val Lys Asn Ala Glu Ile Leu Arg Met Lys Glu Gln Leu Arg Glu
1185                1190                1195                1200
Met Glu Asn Leu Arg Leu Glu Ser Gln Gln Leu Ile Glu Lys Asn Trp
                1205                1210                1215
Leu Leu Gln Gly Gln Leu Asp Asp Ile Lys Arg Gln Lys Glu Asn Ser
            1220                1225                1230
Asp Gln Asn His Pro Asp Asn Gln Gln Leu Lys Asn Glu Gln Glu Glu
        1235                1240                1245
Ser Ile Lys Glu Arg Leu Ala Lys Ser Lys Ile Val Glu Glu Met Leu
    1250                1255                1260
Lys Met Lys Ala Asp Leu Glu Glu Val Gln Ser Ala Leu Tyr Asn Lys
1265                1270                1275                1280
Glu Met Glu Cys Leu Arg Met Thr Asp Glu Val Glu Arg Thr Gln Thr
                1285                1290                1295
Leu Glu Ser Lys Ala Phe Gln Glu Lys Glu Gln Leu Arg Ser Lys Leu
            1300                1305                1310
Glu Glu Met Tyr Glu Glu Arg Glu Arg Thr Ser Gln Glu Met Glu Met
```

```
          1315              1320                    1325
Leu Arg Lys Gln Val Glu Cys Leu Ala Glu Glu Asn Gly Lys Leu Val
    1330              1335                1340

Gly His Gln Asn Leu His Gln Lys Ile Gln Tyr Val Val Arg Leu Lys
1345              1350              1355                  1360

Lys Glu Asn Val Arg Leu Ala Glu Glu Thr Glu Lys Leu Arg Ala Glu
            1365              1370                1375

Asn Val Phe Leu Lys Glu Lys Lys Arg Ser Glu Ser
          1380              1385
```

<210> SEQ ID NO 3
<211> LENGTH: 1128
<212> TYPE: DNA
<213> ORGANISM: Human

<400> SEQUENCE: 3

| | | | | | |
|---|---|---|---|---|---|
| atggcacccg | gctgcaaaac | tgagttacgc | agcgtgacaa | atggtcagtc | taaccaacca | 60 |
| agtaatgaag | gtgatgccat | caaagttttt | gtgcgaattc | gtcctcctgc | agaaagatct | 120 |
| gggtcagctg | atggagagca | gaacttatgc | ttatctgtgc | tgtcctccac | gagtctccgg | 180 |
| ctgcactcca | accctgagcc | caagaccttc | acgtttgatc | atgttgcaga | tgtggatacc | 240 |
| actcaggaat | ctgtattcgc | aactgtggct | aaaagcattg | tggagtcttg | catgagcggt | 300 |
| tataatggta | ccatctttgc | atatggacag | actggctcag | ggaagacatt | tactatgatg | 360 |
| ggaccatctg | aatctgataa | tttttctcat | aacctgagag | gagtaatccc | acgaagtttt | 420 |
| gaatatttgt | tttccttaat | tgatcgtgaa | aagaaaaagg | ctggagctgg | aaagagtttc | 480 |
| ctttgtaagt | gttcctttat | tgaaatctac | aacgagcaga | tatatgatct | actggactct | 540 |
| gcatcggctg | gactgtactt | aagggagcat | atcaagaagg | gagtctttgt | tgttggtgcg | 600 |
| gtggagcagt | ggtaacctc | agctgctgaa | gcctatcagg | tgttgtctgg | aggatggagg | 660 |
| aatagacgtg | tggcatcaac | atcaatgaac | agagaatcgt | ctaggtctca | tgccgtcttt | 720 |
| acaattacaa | tagagtcaat | ggagaaaagt | aatgagattg | tgaatatacg | gacctcccta | 780 |
| ctcaacctgg | tggatttagc | aggatctgaa | aggcaaaaag | atacccatgc | agaagggatg | 840 |
| agattgaagg | aagcaggtaa | cataaatcga | tcattgagct | gcctgggcca | agtgattaca | 900 |
| gcacttgtcg | acgtgggtaa | tggaaaacag | agacatgttt | gctacagaga | ctccaaactt | 960 |
| accttcttac | tacgggattc | ccttggaggt | aatgccaaaa | cagccataat | tgcaaatgtt | 1020 |
| catcctggat | ccaggtgttt | tggggaaacc | ctatcaacac | ttaactttgc | tcaaagagcc | 1080 |
| aagctgatta | aaaacaaggc | actcgagcac | caccaccacc | accactga | | 1128 |

<210> SEQ ID NO 4
<211> LENGTH: 375
<212> TYPE: PRT
<213> ORGANISM: Human

<400> SEQUENCE: 4

```
Met Ala Pro Gly Cys Lys Thr Glu Leu Arg Ser Val Thr Asn Gly Gln
1               5                   10                  15

Ser Asn Gln Pro Ser Asn Glu Gly Asp Ala Ile Lys Val Phe Val Arg
            20                  25                  30

Ile Arg Pro Pro Ala Glu Arg Ser Gly Ser Ala Asp Gly Glu Gln Asn
        35                  40                  45

Leu Cys Leu Ser Val Leu Ser Ser Thr Ser Leu Arg Leu His Ser Asn
    50                  55                  60
```

-continued

```
Pro Glu Pro Lys Thr Phe Thr Phe Asp His Val Ala Asp Val Asp Thr
 65                  70                  75                  80

Thr Gln Glu Ser Val Phe Ala Thr Val Ala Lys Ser Ile Val Glu Ser
                 85                  90                  95

Cys Met Ser Gly Tyr Asn Gly Thr Ile Phe Ala Tyr Gly Gln Thr Gly
            100                 105                 110

Ser Gly Lys Thr Phe Thr Met Met Gly Pro Ser Glu Ser Asp Asn Phe
        115                 120                 125

Ser His Asn Leu Arg Gly Val Ile Pro Arg Ser Phe Glu Tyr Leu Phe
    130                 135                 140

Ser Leu Ile Asp Arg Glu Lys Glu Lys Ala Gly Ala Gly Lys Ser Phe
145                 150                 155                 160

Leu Cys Lys Cys Ser Phe Ile Glu Ile Tyr Asn Glu Gln Ile Tyr Asp
                165                 170                 175

Leu Leu Asp Ser Ala Ser Ala Gly Leu Tyr Leu Arg Glu His Ile Lys
            180                 185                 190

Lys Gly Val Phe Val Val Gly Ala Val Glu Gln Val Val Thr Ser Ala
        195                 200                 205

Ala Glu Ala Tyr Gln Val Leu Ser Gly Gly Trp Arg Asn Arg Arg Val
    210                 215                 220

Ala Ser Thr Ser Met Asn Arg Glu Ser Ser Arg Ser His Ala Val Phe
225                 230                 235                 240

Thr Ile Thr Ile Glu Ser Met Glu Lys Ser Asn Glu Ile Val Asn Ile
                245                 250                 255

Arg Thr Ser Leu Leu Asn Leu Val Asp Leu Ala Gly Ser Glu Arg Gln
            260                 265                 270

Lys Asp Thr His Ala Glu Gly Met Arg Leu Lys Glu Ala Gly Asn Ile
        275                 280                 285

Asn Arg Ser Leu Ser Cys Leu Gly Gln Val Ile Thr Ala Leu Val Asp
    290                 295                 300

Val Gly Asn Gly Lys Gln Arg His Val Cys Tyr Arg Asp Ser Lys Leu
305                 310                 315                 320

Thr Phe Leu Leu Arg Asp Ser Leu Gly Gly Asn Ala Lys Thr Ala Ile
                325                 330                 335

Ile Ala Asn Val His Pro Gly Ser Arg Cys Phe Gly Glu Thr Leu Ser
            340                 345                 350

Thr Leu Asn Phe Ala Gln Arg Ala Lys Leu Ile Lys Asn Lys Ala Leu
        355                 360                 365

Glu His His His His His His
    370                 375

<210> SEQ ID NO 5
<211> LENGTH: 1230
<212> TYPE: DNA
<213> ORGANISM: Human

<400> SEQUENCE: 5
atggcacccg gctgcaaaac tgagttacgc agcgtgacaa atggtcagtc taaccaacca      60
agtaatgaag gtgatgccat caagttttt gtgcgaattc gtcctcctgc agaaagatct     120
gggtcagctg atggagagca gaacttatgc ttatctgtgc tgtcctccac gagtctccgg     180
ctgcactcca accctgagcc caagaccttc acgtttgatc atgttgcaga tgtggatacc     240
actcaggaat ctgtattcgc aactgtggct aaaagcattg tggagtcttg catgagcggt     300
```

-continued

```
tataatggta ccatctttgc atatggacag actggctcag ggaagacatt tactatgatg     360
ggaccatctg aatctgataa tttttctcat aacctgagag gagtaatccc acgaagtttt     420
gaatatttgt tttccttaat tgatcgtgaa aaagaaaagg ctggagctgg aaagagtttc     480
ctttgtaagt gttcctttat tgaaatctac aacgagcaga tatatgatct actggactct     540
gcatcggctg gactgtactt aagggagcat atcaagaagg gagtctttgt tgttggtgcg     600
gtggagcagg tggtaacctc agctgctgaa gcctatcagg tgttgtctgg aggatggagg     660
aatagacgtg tggcatcaac atcaatgaac agagaatcgt ctaggtctca tgccgtcttt     720
acaattacaa tagagtcaat ggagaaaagt aatgagattg tgaatatacg acctcccta      780 ctcaacctgg tggatttagc aggatctgaa aggcaaaaag atacccatgc agaagggatg     840
agattgaagg aagcaggtaa cataaatcga tcattgagct gcctgggcca agtgattaca     900
gcacttgtcg acgtgggtaa tggaaaacag agacatgttt gctacagaga ctccaaactt     960
accttcttac tacgggattc ccttggaggt aatgccaaaa cagccataat tgcaaatgtt    1020
catcctggat ccaggtgttt tggggaaacc ctatcaacac ttaactttgc tcaaagagcc    1080
aagctgatta aaacaaggc agtagtaaat gaagacaccc aaggaaatgt gagccagctc    1140
caagctgaag tgaagaggct caaagaacaa ctggcggagc ttgcttcagg acagacacca    1200
ccactcgagc accaccacca ccaccactga                                      1230
```

<210> SEQ ID NO 6
<211> LENGTH: 409
<212> TYPE: PRT
<213> ORGANISM: Human

<400> SEQUENCE: 6

```
Met Ala Pro Gly Cys Lys Thr Glu Leu Arg Ser Val Thr Asn Gly Gln
 1               5                  10                  15

Ser Asn Gln Pro Ser Asn Glu Gly Asp Ala Ile Lys Val Phe Val Arg
            20                  25                  30

Ile Arg Pro Pro Ala Glu Arg Ser Gly Ser Ala Asp Gly Glu Gln Asn
        35                  40                  45

Leu Cys Leu Ser Val Leu Ser Ser Thr Ser Leu Arg Leu His Ser Asn
    50                  55                  60

Pro Glu Pro Lys Thr Phe Thr Phe Asp His Val Ala Asp Val Asp Thr
65                  70                  75                  80

Thr Gln Glu Ser Val Phe Ala Thr Val Ala Lys Ser Ile Val Glu Ser
                85                  90                  95

Cys Met Ser Gly Tyr Asn Gly Thr Ile Phe Ala Tyr Gly Gln Thr Gly
            100                 105                 110

Ser Gly Lys Thr Phe Thr Met Met Gly Pro Ser Glu Ser Asp Asn Phe
        115                 120                 125

Ser His Asn Leu Arg Gly Val Ile Pro Arg Ser Phe Glu Tyr Leu Phe
    130                 135                 140

Ser Leu Ile Asp Arg Glu Lys Glu Lys Ala Gly Ala Gly Lys Ser Phe
145                 150                 155                 160

Leu Cys Lys Cys Ser Phe Ile Glu Ile Tyr Asn Glu Gln Ile Tyr Asp
                165                 170                 175

Leu Leu Asp Ser Ala Ser Ala Gly Leu Tyr Leu Arg Glu His Ile Lys
            180                 185                 190

Lys Gly Val Phe Val Val Gly Ala Val Glu Gln Val Val Thr Ser Ala
        195                 200                 205
```

-continued

```
Ala Glu Ala Tyr Gln Val Leu Ser Gly Gly Trp Arg Asn Arg Arg Val
        210                 215                 220

Ala Ser Thr Ser Met Asn Arg Glu Ser Ser Arg Ser His Ala Val Phe
225                 230                 235                 240

Thr Ile Thr Ile Glu Ser Met Glu Lys Ser Asn Glu Ile Val Asn Ile
                245                 250                 255

Arg Thr Ser Leu Leu Asn Leu Val Asp Leu Ala Gly Ser Glu Arg Gln
                260                 265                 270

Lys Asp Thr His Ala Glu Gly Met Arg Leu Lys Glu Ala Gly Asn Ile
            275                 280                 285

Asn Arg Ser Leu Ser Cys Leu Gly Gln Val Ile Thr Ala Leu Val Asp
        290                 295                 300

Val Gly Asn Gly Lys Gln Arg His Val Cys Tyr Arg Asp Ser Lys Leu
305                 310                 315                 320

Thr Phe Leu Leu Arg Asp Ser Leu Gly Gly Asn Ala Lys Thr Ala Ile
                325                 330                 335

Ile Ala Asn Val His Pro Gly Ser Arg Cys Phe Gly Glu Thr Leu Ser
                340                 345                 350

Thr Leu Asn Phe Ala Gln Arg Ala Lys Leu Ile Lys Asn Lys Ala Val
            355                 360                 365

Val Asn Glu Asp Thr Gln Gly Asn Val Ser Gln Leu Gln Ala Glu Val
        370                 375                 380

Lys Arg Leu Lys Glu Gln Leu Ala Glu Leu Ala Ser Gly Gln Thr Pro
385                 390                 395                 400

Pro Leu Glu His His His His His His
                405
```